United States Patent
Shojaei et al.

(10) Patent No.: US 7,011,846 B2
(45) Date of Patent: Mar. 14, 2006

(54) ORAL CAPSULE FORMULATION WITH INCREASED PHYSICAL STABILITY

(75) Inventors: Amir H. Shojaei, Gaithersburg, MD (US); Scott A. Ibrahim, Burtonville, MD (US); Beth A. Burnside, Bethesda, MD (US)

(73) Assignee: Shire Laboratories, Inc., Rockville, MD (US)

( * ) Notice: Subject to any disclaimer, the term of this patent is extended or adjusted under 35 U.S.C. 154(b) by 38 days.

(21) Appl. No.: 10/324,954

(22) Filed: Dec. 20, 2002

(65) Prior Publication Data
US 2003/0124182 A1 Jul. 3, 2003

Related U.S. Application Data

(60) Provisional application No. 60/342,430, filed on Dec. 21, 2001.

(51) Int. Cl.
*A61K 9/48* (2006.01)
(52) U.S. Cl. .......................... 424/451; 424/452
(58) Field of Classification Search ........... 424/450, 424/451, 452, 454
See application file for complete search history.

(56) References Cited

U.S. PATENT DOCUMENTS

| 4,339,428 | A | | 7/1982 | Tencza |
| 4,397,848 | A | * | 8/1983 | Bosies et al. ............... 514/183 |
| 5,028,432 | A | | 7/1991 | Chopra et al. |
| 5,431,916 | A | | 7/1995 | White |
| 5,538,737 | A | * | 7/1996 | Leonard et al. ............. 424/451 |
| 5,741,512 | A | * | 4/1998 | Hauer et al. ................. 424/450 |
| 5,776,957 | A | * | 7/1998 | Crooks et al. .............. 514/343 |
| 6,174,547 | B1 | * | 1/2001 | Dong et al. .................. 424/463 |
| 6,267,985 | B1 | * | 7/2001 | Chen et al. .................. 424/451 |
| 2002/0032220 | A1 | * | 3/2002 | Al-Ghazawi et al. ........ 514/321 |

FOREIGN PATENT DOCUMENTS

EP 0 757 911 A1 * 2/1997

* cited by examiner

*Primary Examiner*—S. Tran
(74) *Attorney, Agent, or Firm*—Raj Bawa

(57) ABSTRACT

A formulation for a stabilized capsule for oral administration of a hydrophobic pharmaceutically active agent; comprising a non-aqueous solubilizer selected from 2-pyrrolidone, N-alkylpyrrolidones and combinations thereof; and a capsule stabilizing agent selected from mono-, di- and triglycerides, mono- and di-fatty esters of polyethylene glycol, fatty acids and combinations thereof wherein capsule integrity is maintained for at least 24 hours is disclosed.

9 Claims, No Drawings

ORAL CAPSULE FORMULATION WITH INCREASED PHYSICAL STABILITY

This applications claims the benefit of Provisional Application No. 60/342,430, filed Dec. 21, 2001.

FIELD OF THE INVENTION

The present invention relates to an oral capsule formulation with increased physical stability.

BACKGROUND OF THE INVENTION

It is generally accepted that many of the new pharmaceutically active molecules are insoluble or poorly soluble in water. In order to improve the bioavailability of drugs that exhibit dissolution rate limited oral absorption profiles or to simplify the formulation process, it often becomes necessary to administer the drug in form of a solution or a suspension. Such an approach would then mandate the use of suitable solubilizers in which the pharmaceutical active agent can be fully or partially dissolved. The liquid formulation would then have to be encapsulated in a suitable capsule shell (i.e., hard gelatin, soft gelatin, HPMC hard shell, etc.) to be administered as a solid dosage form. There is often the problem of lack of capsule shell integrity in presence of effective non-aqueous solubilizers such as N-methyl-2-pyrrolidone (NMP) and pyrrolidone derivatives. The capsule shell is either completely dissolved in the solubilizer or it softens as a result of the strong solubilizing properties of the non-aqueous solubilizers. Such deformities would lead to product failures and would limit further dosage formulation development.

The problem of gelatin capsule stability has been addressed by many (see U.S. Pat. Nos. 2,780,355, 4,497,157, 4,777,048, 4,780,316, 5,037,698 and 5,376,381), these innovations have generated different solutions tailored to specific wall destabilizing agents such as hygroscopic and deliquescent components, ethanol, lubricants, salts, etc.

Thus there is a need for oral capsule formulations, containing non-aqueous solubilizers, with increased physical stability.

The present invention provides such a capsule formulation with increased physical stability for oral administration.

SUMMARY OF THE INVENTION

It is an object of the present invention to provide a stabilized capsule for oral administration of a hydrophobic pharmaceutically active agent, containing a composition comprising a non-aqueous solubilizer and a capsule stabilizing agent in an effective amount to improve capsule stability.

A further aspect of the present invention includes a process for improving the stability of a capsule that contains a solubilizer, comprising adding a capsule stabilizing agent in an amount effective to improve capsule integrity.

In an alternate aspect, the invention includes a method for producing a stabilized capsule for oral administration of a pharmaceutical agent comprising:

Mixing a solubilizer and a hydrophobic pharmaceutically active agent;

Incorporating the capsule stabilizing agent to the result of the first step;

Incorporating the result of the second step in a capsule;

wherein the capsule stabilizing agent is in an amount effective to improve capsule stability.

Another aspect of the invention is a pharmaceutical composition intended for oral administration, characterized in that it contains a hydrophobic pharmaceutically active agent, a solubilizer and a capsule stabilizing agent, enclosed in a capsule.

The invention includes a pharmaceutical dosage unit form comprising hydrophobic pharmaceutically active agent, a non-aqueous solubilizer selected from 2-pyrrolidone, $N-C_{1-4}$ alkylpyrrolidones or mixtures thereof and a capsule stabilizing agent selected from fatty esters of glycerol, fatty esters of polyethylene glycol, fatty esters of propylene glycol, fatty acids or mixtures thereof.

In an alternate embodiment of the present invention a pharmaceutical dosage unit form comprising hydrophobic pharmaceutically active agent solubilized in N-methyl-2-pyrrolidone in combination with at least one stabilizing agent selected from $C_{8-10}$ fatty acids, Labrasol(R), Capmul MCM(R), Captex 200 (R), Captex 300 (R) Miglyol (R) and combinations thereof is disclosed.

DETAILED DESCRIPTION OF THE INVENTION

By using appropriate amounts of mono-, di- and triglycerides, mono- and di-fatty esters of polyethylene glycol, fatty acids or mixtures, gelatin capsule shells will stabilize in presence of liquid formulations containing solubilizers such as NMP. Thus, the selection of stabilizing agent such as mono-, di- and triglycerides, mono- and di-fatty esters of polyethylene glycol, fatty acids or mixtures of stabilizing agent in appropriate amounts, allows for formulations to contain a solubilizer such as NMP, without causing damage to the capsule.

Solubilizers such as NMP have reactive functionalities that are capable of forming complexes with molecules in order to enhance their solubility. It is possible that in the case of capsule shell, this ability to form complexes may affect the gelatin of the shell and affect the integrity of the shell with time. The present invention includes the use of stabilizers that will interfere with the complex formation abilities of the solubilizer. The invention includes stabilizers capable of forming complexes with molecules.

It is an object of the present invention to provide a formulation for a stabilised capsule for oral administration of a hydrophobic pharmaceutically active agent, containing a composition comprising a non-aqueous solubilizer and a capsule stabilizing agent in an effective amount to improve capsule stability.

As used in this application, the term "capsule" represents a shell for packaging a drug, a vitamin, a nutritional supplement, a cosmeceutical, or a mixture for oral use. Non-limiting examples of capsule include: Hard gelatine capsule, soft gelatin capsule and HPMC hard shell.

The term "capsule stabilizing agent" means a compound reducing (or preventing) the physical or chemical alteration of a capsule in contact with a non-aqueous solubilizer. It will be appreciated by one skilled in the art that the stabilizing agent will be chosen in order to avoid detrimental interaction or reaction with the other components or reduce the solubility of pharmaceutically active agent.

The term "Non-aqueous solubilizer" means a substance, useful for dissolving a hydrophobic pharmaceutically active agent, susceptible to dissolve or alter the inner wall of a capsule. Mixtures of solubilizers are also within the scope of the invention. Except as indicated, these compounds are readily available from standard commercial sources.

The amount of solubilizer that can be included in compositions of the present invention is not particularly limited. Of course, when such compositions are administered to a patient, the amount of a given solubilizer is limited to a bioacceptable amount, the solubility of the Hydrophobic pharmaceutically active agents and the size of the capsule being used, which are readily determined by one skilled in the art.

The terms "Stabilised capsule" or "capsule stability" refer to a capsule maintaining its ability to hold its content without leakage over a suitable period of time. Non-limiting examples of "suitable period of time" are manufacturing time and storage time.

The term "fatty ester of glycerol" means a glycerol acylated with a fatty acid. It is meant to include mono-fatty ester, di-fatty ester and tri-fatty ester of glycerol.

The term "fatty ester of polyethylene glycol" means a polyethylene glycol acylated with a fatty acid.

It is meant to include mono-fatty ester and di-fatty ester of polyethylene glycol.

The term "fatty ester of propylene glycol" means a propylene glycol acylated with a fatty acid.

It is meant to include mono-fatty ester and di-fatty ester of propylene glycol.

As used in this application, the term "Fatty acid" represents a $C_{1-30}$ unbranched or branched, saturated or unsaturated hydrocarbon chain and a terminal carboxyl group.

"Hydrophobic pharmaceutically active agents" suitable for use in the pharmaceutical compositions of the present invention are not particularly limited. Hydrophobic pharmaceutically active agents are compounds with little or no water solubility (ie., water solubility of the unionised form). Hydrophobic pharmaceutically active agents useful in the present invention have water solubility of less than about 1% by weight, and typically less than about 0.1% or 0.01% by weight. Such hydrophobic pharmaceutically active agents can be any agents having therapeutic or other value when administered to an animal, particularly to a mammal, such as drugs, nutrients, and cosmetics (cosmeceuticals). It is appreciated that mixtures of hydrophobic pharmaceutically active agent may also be used. The amount of hydrophobic pharmaceutically active agent is not specifically restricted but may be any amount convenient for pharmaceutical purpose.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain., branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

In one embodiment, the invention includes non-aqueous solubilizer such as alcohols, polyols, amides, esters and mixtures.

In another embodiment, the non-aqueous solubilizer is an alcohol or polyol chosen from ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives, and mixtures.

In a further embodiment, the invention includes non-aqueous solubilizer such as ester chosen from ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, delta-valerolactone and isomers thereof, beta-butyrolactone and isomers, and mixtures.

In still a further embodiment, the invention includes non-aqueous solubilizer such as amide chosen from 2-pyrrolidone, 2-piperidone, epsilon-caprolactam, N-alkylpyrrolidone, N-hydroxyalkylpyrrolidone, N-alkylpiperidone, N-alkylcaprolactam, dimethylacetamnide, polyvinylpyrrolidone, and mixtures.

In another embodiment, the non-aqueous solubilizer is chosen from 2-pyrrolidone or N-alkylpyrrolidone wherein the alkyl group has 1 to 4 carbon atoms. The N-alkylpyrrolidone may be chosen from N-Methyl-2-Pyrrolidone, N-Ethyl-2-pyrrolidone, N-Propyl-2-pyrrolidone, N-Isopropyl-2-pyrrolidone, N-Butyl-2-pyrrolidone, and N-(2-Hydroxyethyl)-2-pyrrolidone.

In one embodiment, the non-aqueous solubilizer is N-methylpyrrolidone. N-methylpyrrolidone is also known as 1-methylpyrrolidinone, N-methyl-2-pyrrolidinone, 1-methyl-5-pyrrolidinone, methylpyrrolidinone, N-methyl pyrrolidinone, methylpyrrolidinone, N-Methyl-2-pyrrolidone, M-pyrol, NMP or mixtures thereof.

According to a further aspect the invention includes capsule stabilizing agent such as fatty ester of glycerol, fatty ester of polyethylene glycol, fatty ester of propylene glycol, fatty acid, Labrasol(R), Capmul MCM(R), Captex 200 (R), Captex 300 (R) or mixtures thereof.

In another embodiment, the capsule stabilizing agent is chosen from $C_{6-18}$ fatty ester of glycerol, $C_{6-18}$ fatty ester of polyethylene glycol, $C_{6-18}$ fatty ester of propylene glycol, $C_{6-18}$ fatty acid, Labrasol®, Capmul MCM®, Captex 200 ®, Captex 300 ®, Miglyol ® or mixtures thereof.

In another embodiment, the capsule stabilizing agent is chosen from $C_{6-12}$ fatty ester of glycerol, C6-12 fatty ester of polyethylene glycol, $C_{6-12}$ fatty ester of propylene glycol, $C_{6-12}$ fatty acid, Labrasol(R), Capmul MCM(R), Captex 200 (R), Captex 300 (R), or mixture thereof.

In a further embodiment, the capsule stabilizing agent is chosen from $C_{8-10}$ fatty acid, Labrasol(R), Capmul MCM (R), Captex 200 (R), Captex 300 (R) or a mixture.

In one embodiment, the capsule stabilizing agent is present in an amount of from about 5% to about 200% by weight with respect to the non-aqueous solubilizer.

In one embodiment, the capsule stabilizing agent is present in an amount of from about 10% to about 150% by weight with respect to the non-aqueous solubilizer.

In a further embodiment, the capsule stabilising agent is present in an amount of about 20% to about 100% by weight with respect to the non-aqueous solubilizer.

An aspect of the present invention includes a formulation for a stabilised capsule for oral administration of a hydrophobic pharmaceutically active agent, containing a composition comprising a non-aqueous solubilizer, a capsule stabilising agent in an effective amount to improve capsule stability and a hydrophobic pharmaceutically active agent.

In one embodiment, the invention includes hydrophobic pharmaceutically active agent chosen from a drug, a vitamin, a nutritional supplement, a cosmeceutical, or mixtures thereof.

In one embodiment, the hydrophobic pharmaceutically active agent is chosen from:

analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, .beta.-blockers, cardiac inotropic agents, corticosteroids, diuretics, anti-parkinsonian agents, gastro-intestinal agents, histamine $H_1$ and $H_2$ receptor antagonists, keratolytics, lipid regulating agents, anti-anginal agents, nutritional agents, opioid analgesics, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, or mixtures thereof.

In another embodiment, the hydrophobic pharmaceutically active agent is chosen from:

Troxatyl(R), fenofibrate, etoposide, aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenaminc acid, mefenamic acid, nabumetone, naproxen, oxaprozin, oxyphenbutazone, phenylbutazone, piroxicam, rofecoxib, sulindac, tetrahydrocannabinol, tramadol, tromethamine, albendazole, bephenium hydroxynaphthoate, cambendazole, dichlorophen, ivermectin, mebendazole, oxamniquine, oxfendazole, oxantel embonate, praziquantel, pyrantel embonate and thiabendazole, amiodarone HCl, disopyramide, flecainide acetate and quinidine sulfate, zileuton, zafirlukast, terbutaline sulfate, montelukast, albuterol, alatrofloxacin, azithromycin, baclofen, benzathine penicillin, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, vancomycin, abacavir, amprenavir, delavirdine, efavirenz, indinavir, lamivudine, nelfinavir, nevirapine, ritonavir, saquinavir, stavudine, cilostazol, clopidogrel, dicumarol, dipyridamole, nicoumalone, oprelvekin, phenindione, ticlopidine, tirofiban, amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, venlafaxine HCl, acetohexamide, chlorpropamide, glibenclamide, gliclazide, glipizide, glimepiride, miglitol, pioglitazone, repaglinide, rosiglitazone, tolazamide, tolbutamide, troglitazone, beclamide, carbamazepine, clonazepam, ethotoin, felbamate, fosphenytoin sodium, lamotrigine, methoin, methsuximide, methylphenobarbitone, oxcarbazepine, paramethadione, phenacemide, phenobarbitone, phenytoin, phensuximide, primidone, sulthiame, tiagabine HCl, topiramate, valproic acid, vigabatrin, amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole, undecenoic acid, allopurinol, probenecid and sulphinpyrazone, amlodipine, benidipine, benezepril, candesartan, captopril, darodipine, dilitazem HCl, diazoxide, doxazosin HCl, enalapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, valsartan, amodiaquine, chloroquine, chlorproguanil HCl, halofantrine HCl, mefloquine HCl, proguanil HCl, pyrimethamine, quinine sulfate, dihydroergotamine mesylate, ergotamine tartrate, frovatriptan, methysergide maleate, naratriptan HCl, pizotifen maleate, rizatriptan benzoate, sumatriptan succinate, zolmitriptan, atropine, benzhexol HCl, biperiden, ethopropazine HCl, hyoscyamine, mepenzolate bromide, oxyphencyclimine HCl, tropicamide, aminoglutethimide, amsacrine, azathioprine, bicalutamide, bisantrene, busulfan, camptothecin, capecitabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, toremifene citrate, atovaquone, benznidazole, clioquinol, decoquinate, diiodohydroxyquinoline, diloxanide furoate, dinitolmide, furazolidone, metronidazole, nimorazole, nitrofurazone, ornidazole, tinidazole, carbimazole, paracalcitol, propylthiouracil, benzonatate, alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, flupenthixol decanoate, fluphenthixol decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, pseudoephedrine, quetiapine, risperidone, sertindole, sulpiride, temazepam, thioridazine, triazolam, zolpidem, zopiclone, acebutolol, alprenolol, atenolol, labetalol, metoprolol, nadolol, oxprenolol, pindolol, propranolol, amrinone, digitoxin, digoxin, enoximone, lanatoside C, medigoxin, beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone, triamcinolone, acetazolamide, amiloride, bendroflumethiazide, bumetanide, chlorothiazide, chlorthalidone, ethacrynic acid, frusemide, metolazone, spironolactone, triamterene, bromocriptine mesylate, lysuride maleate, pramipexole, ropinirole HCl, tolcapone, bisacodyl, cimetidine, cisapride, diphenoxylate HCl, domperidone, famotidine, lanosprazole, loperamide, mesalazine, nizatidine, omeprazole, ondansetron HCL, rabeprazole sodium, ranitidine HCl, sulphasalazine, acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, terfenadine, acetretin, calciprotriene, calcifediol, calcitriol, cholecalciferol, ergocalciferol, etretinate, retinoids, targretin, tazarotene, atorvastatin, bezafibrate, cerivastatin, ciprofibrate, clofibrate, fenofibrate, fluvastatin, gemfibrozil, pravastatin, probucol, simvastatin, dantrolene sodium, tizanidine HCl, amyl nitrate, glyceryl trinitrate, isosorbide dinitrate, isosorbide mononitrate, pentaerythritol tetranitrate, calcitriol, carotenes, dihydrotachysterol, essential fatty acids, non-essential fatty acids, phytonadiol, vitamin A, vitamin $B_2$, vitamin D, vitamin E, vitamin K, codeine, dextropropoxyphene, diamorphine, dihydrocodeine, fentanyl, meptazinol, methadone, morphine, nalbuphine, pentazocine, clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone, tibolone, amphetamine, dexamphetamine, dexfenfluramine, fenfluramine, mazindol, becaplermin, donepezil HCl, L-thryroxine, methoxsalen, verteporfin, physostigmine, pyridostigmine, raloxifene HCl, sibutramine HCl, sildenafil citrate, tacrine, tamsulosin HCl, and tolterodine.

In another embodiment, the hydrophobic pharmaceutically active agent is chosen from from: Troxatyl(R), fenofibrate, etoposide and carbamazepine.

In still another embodiment, the hydrophobic pharmaceutically active agent is fenofibrate.

The invention includes a pharmaceutical dosage unit form comprising hydrophobic pharmaceutically active agent, a non-aqueous solubilizer selected from 2-pyrrolidone, N-alkylpyrrolidone or mixtures thereof and a capsule stabilizing agent selected from fatty esters of glycerol, fatty esters of polyethylene glycol, fatty esters of propylene glycol, fatty acids or mixtures thereof and the capsule stabilizing agent is chosen from $C_{6-18}$ fatty ester of glycerol, $C_{6-18}$ fatty ester of polyethylene glycol, $C_{6-18}$ fatty ester of propylene glycol, $C_{6-18}$ fatty acid, Labrasol(R), Capmul MCM(R), Captex 200 (R), Captex 300 (R) Miglyol (R) or mixtures thereof. The invention also includes solubilizer selected from N-alkylpyrrolidone wherein the alkyl group has 1 to 4 carbon atoms. The invention includes solubilizer selected from N-Methyl-2-Pyrrolidone, N-Ethyl-2-pyrrolidone, N-Propyl-2-pyrrolidone, N-Isopropyl-2-pyrrolidone, N-Butyl-2-pyrrolidone, N-(2-Hydroxyethyl)-2-pyrrolidone and mixtures thereof; and the capsule stabilizing agent is chosen from $C_{8-10}$ fatty acid, Labrasol(R), Capmul MCM(R), Captex 200 (R), Captex 300 (R) or combinations thereof.

The present invention includes a pharmaceutical dosage unit form comprising hydrophobic pharmaceutically active agent solubilized in 2-pyrrolidone, 2-piperidone, epsiloncaprolactam, N-alkylpyrrolidone, N-hydroxyalkylpyrrolidone, N-alkylpiperidone, N-alkylcaprolactam, dimethylacetamnide, polyvinylpyrrolidone, and mixtures thereof and at least one stabilizing agent selected from $C_{8-10}$ fatty acids, Labrasol(R), Capmul MCM(R), Captex 200 (R), Captex 300 (R) Miglyol (R) and combinations thereof.

The scope of the present invention includes a pharmaceutical dosage unit form comprising hydrophobic pharmaceutically active agent solubilized in N-methyl-2-pyrrolidone in combination with at least one stabilizing agent selected from $C_{8-10}$ fatty acids, Labrasol(R), Capmul MCM (R), Captex 200 (R), Captex 300 (R) and combinations thereof.

It is appreciated that mixtures of hydrophobic pharmaceutically active agent may also be used in an embodiment of the invention.

In one embodiment, the hydrophobic pharmaceutically active agent is present in an amount of from about 1% to about 200% by weight with respect to the non-aqueous solubilizer.

In a further embodiment, the hydrophobic pharmaceutically active agent is present in an amount of from about 10% to about 150% by weight with respect to the non-aqueous solubilizer.

In still a further embodiment, the hydrophobic pharmaceutically active agent is present in an amount of about 100% by weight with respect to the non-aqueous solubilizer.

It will also be appreciated by a person of skill that additional agents such as antioxidants, thickening agents, suspending agents may be added to the composition of the invention if desired. It will be appreciated by one skilled person that the additional components will be chosen in order to avoid detrimental interaction or reaction with the other components or reduce the solubility of the hydrophobic pharmaceutically active agent.

A further aspect of the present invention includes a process for improving the stability of a capsule that contains a solubilizer, comprising adding a capsule stabilizing agent in an amount effective to maintain capsule integrity.

In an alternate embodiment, the invention includes a method for producing a stabilized capsule for oral administration of a pharmaceutical agent comprising:

Mixing a solubilizer and a hydrophobic pharmaceutically active agent;

Incorporating the capsule stabilizing agent to the result of the first step;

Incorporating the result of the second step in a capsule;

wherein the capsule stabilizing agent is present in an amount effective to improve capsule stability. The process may additionally include a capsule sealing step such as gelatin banding or microspray sealing using small amounts of hydroalcoholic solution to prevent leakage.

Another aspect of the invention is a pharmaceutical composition intended for oral administration, characterized in that it contains a hydrophobic pharmaceutically active agent, a solubilizer and a capsule stabilizing agent, enclosed in a capsule.

The advantages and embodiments of the present invention are further illustrated in the examples that follow.

EXAMPLES

Example 1

Preparation of Compositions and Stability Studies.

NMP was filled into a size 0 hard gelatin capsule in order to determine the effect of NMP on the integrity of the shell. Within minutes, the capsule cracked causing the content to leak out.

To stabilize the capsule shell in presence of solution of NMP, various capsule stabilizing agents were studied for their stability inducing properties. Stabilizing agents were each incorporated into NMP separately. Formulations were prepared by mixing or dissolving each excipient in a vial containing NMP with a 1:1 ratio (wt/wt). The solutions were then encapsulated into size 0 hard gelatin capsules and banded to prevent leakage of the fill contents. Capsules were stored at ambient environment and observations were made at regular time intervals for leakage and capsule shell cracking. The results are shown in Table 1.

TABLE 1

| Entry | Solubilizer | Stabilizing agent/ Chemical Name | Trade Name/ Other Name | Observations |
|---|---|---|---|---|
| #1 | NMP | — | — | Capsule shell cracked |
| #2 | NMP | Caprylocaproyl macrogol-8 glycerides | Labrasol ® | Capsule shell intact |
| #3 | NMP | Caprylic/Capric Glycerides | Capmul ® MCM | Capsule shell intact |
| #4 | NMP | Propylene Glycol dicaprylate/Dicaprate | Captex ® 200 | Capsule shell intact |
| #5 | NMP | Glyceryl tricaprylate/Caprate | Captex ® 300 | Capsule shell intact |
| #6 | NMP | Octanoic acid | Caprylic Acid | Capsule shell intact |
| #7 | NMP | Decanoic acid | Capric Acid | Capsule shell intact |
| #8 | NMP | Polyoxyl 40 Hydrogenated Castor Oil | Cremophor ® RH 40 | Capsule shell cracked |
| #9 | NMP | Polyoxyl 23 lauryl ether | Brij ® 35 | Capsule shell cracked |
| #10 | NMP | (Z)-Sorbitan mono-9-octadecenoate | Span 80 ® | Capsule shell cracked |
| #11 | NMP | α-Hydro-ω-hydroxy-poly (oxy-1,2-ethanediyl) | Carbowax ® | Capsule shell cracked |
| #12 | NMP | Glycerol esters of saturated $C_8$–$C_{18}$ fatty acids | Gelucire ® 33/01 | Capsule shell cracked |

Entries 2–7 provided effective stability improvement for the 5 capsule shells.

Note:
Labrasol is a trade name for a caprylocaproyl macrogol-8 glyceride blend marketed by Gattefosse Corp.
Captex 200 is a trade name for a propylene Glycol Dicaprylate/Dicaprate blend marketed by Abitec Corp.
Captex 300 is a trade name for a Glyceryl tricaprylate/caprate blend marketed by Abitec Corp.
Gelucire 33/01 is a trade name for a blend of Glycerol esters of saturated C8–C18 fatty acids, marketed by Gattefosse Corp.
Cremophor RH40 is a trade name for PEG-n-Hydrogenated Castor Oil and marketed by BASF Corp.
Span 80 is a trade name for sorbitan monooleate marketed by ICI Chemical.
Carbowax 400 is α-Hydro-ω-hydroxy-poly (oxy-1,2-ethanediyl) marketed by Dow Chemical Company
Brij 35 is a trade name for Polyoxyl 23 lauryl ether marketed by Sigma Corp.
Capmul MCM is the trade name for Caprylic/Capric Glycerides blend marketed by Abitec Corp.

Example 2

Preparation of Compositions and Stability Studies.

In order to further demonstrate the stabilizing affect of the capsule stabilizing agents, different compositions containing various ratios of NMP to stabilizing agents were encapsulated in gelatin capsules. Stabilizing agents were each incorporated into NMP separately. Formulations were prepared by mixing or dissolving each stabilizing agent in a vial containing NMP. The solutions were then encapsulated into size 0 hard gelatin capsules and banded to prevent leakage of the fill contents. Capsules were stored at ambient environment and observations were made at regular time intervals for leakage and capsule shell cracking. The results are shown in Table 2.

TABLE 2

| Stabilizing agent/ Chemical Name | Trade Name/ Other Name | NMP: Stabilizing agent Ratio (wt:wt) | Observations |
|---|---|---|---|
| Caprylocaproyl macrogol-8 glycerides | Labrasol ® | 1:0.2 | Capsule shell intact |
| Caprylocaproyl macrogol-8 glycerides | Labrasol ® | 1:0.5 | Capsule shell intact |
| Caprylic/Capric Glycerides | Capmul MCM ® | 1:0.2 | Capsule shell intact |
| Caprylic/Capric Glycerides | Capmul MCM ® | 1:0.5 | Capsule shell intact |
| Octanoic acid | Caprylic Acid | 1:0.2 | Capsule shell intact |
| Octanoic acid | Caprylic Acid | 1:0.5 | Capsule shell intact |
| Decanoic acid | Capric Acid | 1:0.2 | Capsule shell intact |
| Decanoic acid | Capric Acid | 1:0.5 | Capsule shell intact |
| Lauroyl macrogol-32 glycerides | Gelucire ® 44/14 | 1:0.2 | Capsule shell intact |
| Lauroyl macrogol-32 glycerides | Gelucire ® 44/14 | 1:0.5 | Capsule shell intact |

TABLE 3

Capsule stability using formulations containing NMP with various excipients
Capsules were kept at Room temperature and the temperature was not controlled. Capsules were observed for one year.

| Excipient | Ratios | Capsules Used | Time | Results |
|---|---|---|---|---|
| Caprylic Acid:NMP | 1:1 | Size 0 Capsugel capsules | 1 week 1 month 3 months 6 months | No Change* |
| | 0.5:1 | 1 ml Softgel capsule | 1 year | |
| Capric Acid:NMP | 1:1 | Size 0 Capsugel capsules | 1 week 1 month 3 months 6 months | No Change** |
| | 0.5:1 | 1 ml Softgel capsule | 1 year | |
| Capric:Caprylic: NMP | 0.5:0.5:1 | Size 0 Capsugel capsules | 1 week 1 month 3 months 6 months | No Change** |
| | 0.25:0.25:1 | 1 ml Softgel capsule | 1 year | |
| Gelucire 50/13:NMP | 1:1 | Size 0 Capsugel capsules | 1 week 1 month 3 months 6 months 1 year | No Change** |
| Gelucire 44/14:NMP | 1:1 | Size 0 Capsugel capsules | 1 week 1 month 3 months 6 months 1 year | No Change** |

**No physical changes seen with hard gelatin capsules or softgel capsules (color changes, brittleness, shape, leakage).

The capsules containing the formulations in table 3 remained unchanged for one year at room temperature.

The invention claimed is:

1. A stabilized capsule for oral administration of a hydrophobic pharmaceutically active agent; wherein said capsule contains a formulation consisting essentially of a hydrophobic pharmaceutically active agent and a solubilizing composition, wherein said solubilizing composition consists essentially of at least one N-alkylpyrrolidone, and a capsule stabilizing agent selected from mono- and diglycerides, mono- and di-fatty esters of polyethylene glycol, fatty esters of propylene glycol, fatty acids and combinations thereof, wherein the stabilizing agent to the N-alkylpyrrolidone weight ratio is from about 1:20 to about 2:1 and wherein said amount of stabilizing agent is sufficient to maintain capsule wall integrity for at least 24 hours.

2. A capsule according to claim 1 wherein said N-alkylpyrrolidone is selected from the group consisting of N-methyl-2-pyrrolidone, N-ethyl-2-pyrrolidone, N-propyl-2-pyrrolidone, N-isopropyl-2-pyrrolidone, N-butyl-2-pyrrolidone, and mixtures thereof.

3. A capsule according to claim 2 wherein said N-alkylpyrrolidone is N-methyl-2-pyrrolidone.

4. A capsule according to claim 1 wherein the capsule stabilizing agent is present in amounts of from about 10% to about 150% by weight with respect to the non-aqueous solubilizer.

5. A capsule according to claim 4 wherein the capsule stabilizing agent is present in amounts of from about 20% to about 100% by weight with respect to the non-aqueous solubilizer.

6. A capsule according to claim 1 wherein the non-aqueous solubilizer is present in sufficient amounts to maintain the hydrophobic pharmaceutically active agent in solution or suspension.

7. A capsule according to claim 1 wherein the non-aqueous solubilizer is a complexing agent, wherein said complexing agent is N-methyl-2-pyrrolidone.

8. A capsule containing a pharmaceutical dosage unit form consisting essentially of a hydrophobic pharmaceutically active agent and a solubilizing composition, wherein said solubilizing composition consists essentially of a non-aqueous solubilizer selected from at least one N-alkylpyrrolidone and a capsule stabilizing agent selected from mono- and diglycerides, fatty esters of polyethylene glycol, fatty esters of propylene glycol, fatty acids or mixtures thereof, wherein the stabilizing agent to the N-alkylpyrrolidone weight ratio is from 1:20 to about 2:1 and wherein said amount of stabilizing agent is sufficient to maintain capsule wall integrity for at least 24 hours.

9. A formulation for a stabilized capsule for oral administration of a hydrophobic pharmaceutically active agent; wherein said capsule contains a formulation consisting essentially of a hydrophobic pharmaceutically active agent, at least one $N-C_{1-4}$ alkylpyrrolidone non-aqueous solubilizer, and a capsule stabilizing agent selected from mono- and diglycerides, mono- and di-fatty esters of polyethylene glycol, fatty esters of propylene glycol, fatty acids and combinations thereof, wherein the stabilizing agent to the N-alkylpyrrolidone weight ratio is from about 1:20 to about 2:1 and wherein said amount of stabilizing agent is sufficient to maintain capsule wall integrity for at least 24 hours.

* * * * *